(12) United States Patent
Kipp et al.

(10) Patent No.: US 6,479,541 B1
(45) Date of Patent: Nov. 12, 2002

(54) AMIODARONE-CONTAINING PARENTERAL ADMINISTRATION

(75) Inventors: James E. Kipp, Wauconda; Mark J. Doty, Grayslake; Christine L. Rebbeck, Algonquin; Jan Y. Eilert, Wauconda, all of IL (US)

(73) Assignee: Baxter International, Deerfield, IL (US)

( * ) Notice: Subject to any disclaimer, the term of this patent is extended or adjusted under 35 U.S.C. 154(b) by 0 days.

(21) Appl. No.: 09/539,446

(22) Filed: Mar. 30, 2000

(51) Int. Cl.⁷ ............................................. A61K 31/343
(52) U.S. Cl. ....................................... 514/469; 514/557
(58) Field of Search .................. 514/469, 557

(56) References Cited

U.S. PATENT DOCUMENTS

| | | |
|---|---|---|
| 5,234,949 A | 8/1993 | Ehrenpreis et al. |
| 6,030,998 A | 2/2000 | Somberg |
| 6,143,778 A * | 11/2000 | Gautier et al. ............. 514/469 |

FOREIGN PATENT DOCUMENTS

| | | |
|---|---|---|
| FR | WO 97/02031 | 1/1997 |

* cited by examiner

*Primary Examiner*—Frederick Krass
(74) *Attorney, Agent, or Firm*—Mark Buonaiuto; Robert Diehl

(57) ABSTRACT

The present invention provides an amiodarone parenteral solution suitable for intravenous administration without the necessity of dilution. The parenteral solution has an amiodarone concentration from 0.2 to 10 mg/ml and a buffer solution selected from the group consisting of lactate buffer, methanesulfonate buffer, or combinations thereof, the solution having a pH within the range from approximately 2.5–4.5.

9 Claims, No Drawings

AMIODARONE-CONTAINING PARENTERAL ADMINISTRATION

TECHNICAL FIELD

The present invention relates to an amiodarone antiarrhythmic agent and more particularly to a parenteral solution of amiodarone for intravenous infusion.

BACKGROUND OF THE INVENTION

Amiodarone is a type III antiarrhythmic agent that exhibits a broad spectrum of activity. The hydrochloride salt is currently marketed in ampoules suitable for intravenous administration following dilution in dextrose (Cordarone IV, Wyeth-Ayrest). The pH range of the diluted product (measured in the lab) is from 3.8–4.0.

Amiodarone free base has an extremely low estimated intrinsic solubility in water (18 6 ng/mL). The free base is neutral and by protonation with acid is converted to a more water-soluble trialkylammonium ion. However, the hydrochloride salt (used in the current commercial product) is not appreciably soluble in water at moderately low pH (3.8–4.5). Therefore, the commercial formulation contains polysorbate 80 as a surfactant to aid in dissolving and solubilizing the drug. This may be a serious drawback because glycol ethers and their derivatives such as polyethylene glycols (PEGs) or polysorbates (Tweens) are known to contribute to pain on injection, and may also induce anaphylactic reactions. Tween 80 has also been associated with cardiodepression, causing hypotension (Gough et al., "Hypotensive Action of Commercial Intravenous Amiodarone and Polysorbate 80 in Dogs," Journal of Cardiovascular Pharmacology, 1982, 375–380).

U.S. Pat. No. 5,234,949 provides a surfactant-free amiodarone solution packaged in an ampoule suitable for intravenous parenteral administration upon dilution. The '949 Patent discloses using an acetate buffer solution (0.05–0.1 M) to adjust the pH of a 25–75 mg/ml amiodarone solution to be below 4 and more preferably within the range of 3.5–3.8. It also discloses that the concentration of the buffer and the choice of buffering agent are critical for physical stability, i.e., precipitation or gel formation occurred when a 0.2 M acetate, 0.1 M phthalate, or 0.1 M phosphate buffer was used to solubilize the drug.

Patent WO9702031 provides a 1.5–8 wt % surfactant-containing amiodarone solution suitable for parenteral administration. Patent WO9702031 discloses uses a non-ionic hydrophilic surfactant (e.g., Tween 80, Pluronic P94, or Cremophor EL) in combination with an acetate or phosphate buffer solution at a pH from 2.4–3.8 to solubilize the drug.

Neither of these patents, however, discloses using lactic or methanesulfonic acid to solubilize the drug, nor do they describe the use of lactate or methanesulfonate buffer for preparing a surfactant-free amiodarone formulation. In addition, they do not disclose the preparation of a surfactant-free amiodarone parenteral solution suitable for intravenous administration without the necessity of dilution.

SUMMARY OF THE INVENTION

The present invention provides a surfactant-free amiodarone parenteral solution suitable for intravenous administration without the necessity of dilution. The solution contains an active ingredient of amiodarone hydrochloride in a concentration range from 0.2–10 mg/ml and a buffer solution selected from the group consisting of lactate buffer, methanesulfonate buffer or any combination of these two buffers. The solution should have a pH within the range of approximately 2.5–4.5. The solution can also optionally include an osmotic agent such as dextrose, mannitol, sorbitol, glycerol, amino acids such as glycine, or salts such as sodium chloride.

The present invention also provides a method for preparing an amiodarone solution suitable for intravenous administration. The method comprises the steps of: (1) providing an effective ingredient or ingredients of an amiodarone solution; (2) providing distilled water; (3) providing an acid selected from the group consisting of lactic acid and methanesulfonic acid or combination thereof; (4) mixing an effective amount of the lactic acid, methanesulfonic acid or the combination of the two acids with heated, distilled water; (5) solubilizing an effective amount of the active ingredient in the heated water/acid solution; (6) cooling the solution; (7) adjusting the pH of the solution with a suitable pH adjuster to be within the range of from approximately 2.5–4.5; (8) diluting the solution to the final active ingredient concentration. The method can include the optional step of mixing into the solution an osmotic agent such as dextrose, mannitol, sorbitol, glycerol, amino acids, inorganic salts, and any combination of these osmotic adjusters into the solution.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

While the specific embodiments have been illustrated and described, numerous modifications come to mind without significantly departing from the spirit of the invention and the scope of protection is only limited by the scope of the accompanying claims.

According to the present invention, there is provided a parenteral solution containing as an active ingredient a benzofuran drug, which is solubilized by lactic acid, methanesulfonic acid, or any combination thereof. The pH of the solution is adjusted to be within the range of approximately 2.5–4.5. The active ingredient has the following structural formula:

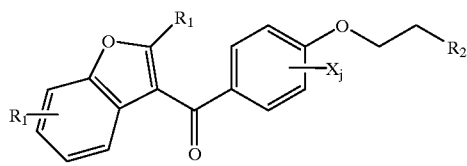

$R_i$ represents one or more groups selected from alkyl, aryl, alkoxy, aryloxy or halogen substituents. $R_1$ represents an alkyl, aryl, alkoxy, aryloxy or halogen substituent, $X_j$ includes one or more iodo or bromo substituents on the phenyl ring. $R_2$ represents a dialkylamino group such as N,N-dimethylamino or N,N-diethylamino. $R_2$ can also be a 1-substituted heterocycle such as 1-morpholinyl, 1-piperazinyl, or 1-piperadinyl.

In a preferred form of the invention the active ingredient is a cardiovascular agent with the following structural formula:

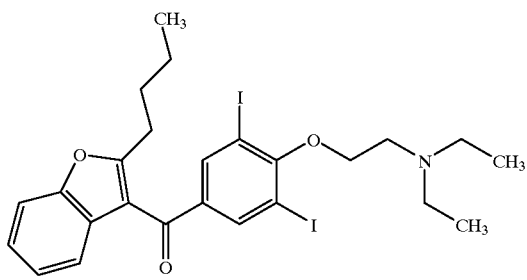

The parenteral solution is prepared by adding a sufficient amount of lactic acid, methanesulfonic acid, or a combination of these acids to distilled, deionized water or Water for Injection, USP. The solution is heated to a temperature of approximately 45–70° C. Amiodarone is mixed into the solution in a sufficient amount so that the concentration is from about 0.2 to 25 mg/ml, and more preferably from 0.5 to 10 mg/ml. The solution is then slightly diluted and cooled to a temperature from approximately 25–35° C. An osmotic agent may be added to the solution at this point in an amount from 100 to 450 mM and more preferably from 150 to 350 mM. The solution is pH adjusted with a suitable pH adjuster (e.g., hydrochloric acid or sodium hydroxide) to a pH from approximately 2.5–4.5. The solution is then diluted to give a final amiodarone concentration from 0.2 to 10 mg/ml with distilled, deionized water or Water for Injection, USP.

Suitable amiodarone hydrochloride is sold by ISOCHEM. The lactic or methanesulfonic acids may be used as the pure compounds or as solutions prepared by suitable dilutions of these acids. Lactic acid may also be heat-treated to hydrolyze any dimers or polymers present in the pure raw material, or in solutions prepared from it. Suitable lactic acid is sold by PURAC under the tradename 90% Lactic Acid, USP. Suitable methanesulfonic acid is sold by Aldrich under the tradename Methanesulfonic Acid. Suitable osmotic agents include dextrose, mannitol, sorbitol, glycerol, amino acids such as glycine, or inorganic salts such as sodium chloride.

The parenteral solutions of the present invention do not contain any non-ionic hydrophilic solubilizing surfactants, such as polyethylene glycols, polysorbates, or polyethylene glycol stearate esters which are known to have adverse pharmacologic effects when injected as a component in an I.V. solution. Nor do the formulations of the present invention contain any organic cosolvents such as propylene glycol or ethanol.

The following are non-limiting examples of the present invention and should not be used to narrow the scope of the present invention.

EXAMPLES

Example 1

Preparation of Amiodarone Formulation using Lactic Acid

To a 20-L jacketed tank reactor was added 8 L of distilled, deionized water. To this was added 400 mL of 20% lactic acid (previously prepared by heat treatment of a diluted 90% lactic acid concentrate to hydrolyze lactic acid dimer). The mixture was brought to 55° C. 36 g of amiodarone hydrochloride was added to the mixture and agitated to dissolution. The mixture was diluted to 16 L and cooled to 30° C. 909.2 g of dextrose was added to the mixture and agitated to dissolution. The mixture was adjusted with sodium hydroxide to a final pH of 3.5. The solution was then diluted to 20 L with distilled, deionized water. This provided a solution having an approximate drug concentration of 1.8 mg/mL.

Example 2

Preparation of Amiodarone Formulation using Methanesulfonic Acid

To a 100 mL beaker was added 30 mL of distilled, deionized water. To this was added 0.1 g of amiodarone hydrochloride. The mixture was brought to 45–60° C. in a hot water bath. The mixture was pH adjusted with methanesulfonic acid and sodium hydroxide (if necessary) to a pH of 3–4.5. (At this point, an osmotic agent such as dextrose, mannitol and glycerol, may optionally be added if desired, and mixed until dissolved) The solution was then diluted to 50 mL with distilled, deionized water. The final concentration of amiodarone hydrochloride was approximately 2 mg/mL.

Formulation Stability

Formulations prepared as described above were found to be stable with respect to drug concentration, pH, and visual particulate when refrigerated or frozen over a 1 year period in glass. These formulations also passed the USP particle limits for parenteral products.

We claim:

1. A parenteral solution for intravenous administration without dilution comprising as an active ingredient, amiodarone in a concentration range from 0.2 to 10 mg/ml and a buffer solution selected from the group consisting of lactate buffer, methanesulfonate buffer, and combinations thereof, the solution being free of surfactant and having a pH within the range of from approximately 2.5 to approximately 4.5.

2. The solution of claim 1 wherein the pH of the solution is adjusted to the range with an acid and wherein the acid for pH adjustment is lactic acid.

3. The solution of claim 1 wherein the buffer is a lactate buffer.

4. The solution of claim 1 wherein the pH of the solution is adjusted to the range with an acid and wherein the acid for pH adjustment is methanesulfonic acid.

5. The solution of claim 1 wherein the buffer is methanesulfonate.

6. The solution of claim 1 further comprising an osmotic agent.

7. The solution of claim 6 wherein the osmotic agent is selected from the group consisting of dextrose, mannitol, sorbitol, glycerol, amino acids, and inorganic salts.

8. A method for preparing an amiodarone intravenous solution for intravenous administration comprising the steps of: providing an amiodarone solution; providing distilled water; providing an acid selected from the group consisting of lactic acid and methanesulfonic acid and combinations thereof; mixing an effective amount of the lactic, methanesulfonic acid, or combinations of these acids, with heated (45–70° C.), distilled water; solubilizing from 0.2–25 mg/ml of the active ingredient (amiodarone) in the heated water/acid solution; cooling the solution; adjusting the pH of the solution with a pH adjuster to be within the range of from approximately 2.5 to approximately 4.5; and, diluting the solution to a final active ingredient concentration.

9. The method of claim 8 further comprising: providing an osmotic agent selected from the group consisting of dextrose, mannitol, sorbitol, glycerol, amino acids, inorganic salts, and combinations thereof, and mixing the osmotic agent into the solution.

* * * * *

UNITED STATES PATENT AND TRADEMARK OFFICE
CERTIFICATE OF CORRECTION

PATENT NO. : 6,479,541 B1
DATED : November 12, 2002
INVENTOR(S) : James E. Kipp, Mark J. Doty, Christine L. Rebbeck and Jan Y. Eilert It is certified that error appears in the above-identified patent and that said Letters Patent is hereby corrected as shown below:

<u>Column 1,</u>
Line 18, delete "18".

Signed and Sealed this

First Day of July, 2003

JAMES E. ROGAN
*Director of the United States Patent and Trademark Office*